United States Patent
Oliver et al.

(10) Patent No.: US 6,575,935 B1
(45) Date of Patent: Jun. 10, 2003

(54) INFUSION SYSTEM WITH IMPROVED CONTROL VALVE

(75) Inventors: Dana A. Oliver, Plymouth, MA (US); Joseph A. Bruno, Jr., Easton, MA (US)

(73) Assignee: Level 1, Inc., Rockland, MA (US)

( * ) Notice: Subject to any disclaimer, the term of this patent is extended or adjusted under 35 U.S.C. 154(b) by 0 days.

(21) Appl. No.: 09/529,414

(22) PCT Filed: Nov. 2, 1998

(86) PCT No.: PCT/US98/22648
§ 371 (c)(1),
(2), (4) Date: Jul. 17, 2000

(87) PCT Pub. No.: WO99/22786
PCT Pub. Date: May 14, 1999

Related U.S. Application Data

(60) Provisional application No. 60/064,234, filed on Nov. 4, 1997.

(51) Int. Cl.[7] .............................................. A61M 37/00
(52) U.S. Cl. ................. 604/141; 604/249; 128/DIG. 12
(58) Field of Search ................................ 604/246, 247, 604/248, 23, 500, 167.01, 167.03, 167.05, 257, 151, 131, 140–141, 147, 99.01, 99.02, 99.04, 249; 251/142, 149, 153, 205–206, 213, 231

(56) References Cited

U.S. PATENT DOCUMENTS

| 3,469,578 A | 9/1969 | Bierman ...................... 128/214 |
| 5,147,310 A | * 9/1992 | Giannini et al. ..... 128/DIG. 12 |
| 5,308,335 A | * 5/1994 | Ross et al. ................... 604/141 |
| 5,318,515 A | 6/1994 | Wilk ............................ 604/30 |
| 5,484,415 A | 1/1996 | Kriesel ........................ 604/132 |
| 5,720,728 A | 2/1998 | Ford ............................ 604/131 |
| 5,743,878 A | 4/1998 | Ross ............................ 604/131 |

* cited by examiner

Primary Examiner—Brian L. Casler
Assistant Examiner—Mark K Han
(74) Attorney, Agent, or Firm—Louis Woo

(57) ABSTRACT

A system and method for pressurizing bags of physiological fluids include a control valve for providing deflation of a bladder that compresses the bags. The toggle portion of the control valve is movable between a first and second position respectively for inflation and deflation of the bladder. When the toggle portion is in the first position, the control valve connects a source of pressurized air to the bladder, and when the toggle portion is in the second position, the control valve allows the bladder to exhaust directly to the atmosphere through an outlet port in the valve. The size of the outlet port is so large that it creates only very little resistance to the discharged air.

20 Claims, 2 Drawing Sheets

INFUSION SYSTEM WITH IMPROVED CONTROL VALVE

CROSS REFERENCE TO RELATED APPLICATION

This application claims priority of U.S. Provisional Application Ser. No. 60/064,234, which was filed on Nov. 4, 1997.

TECHNICAL FIELD

This invention relates to the art of infusion pumps. In particular, the invention relates to a method and apparatus for allowing rapid deflation of a pressure infusion bladder.

BACKGROUND

The use of infusion devices for supply of intravenous fluids to patients is well known. As well, it is known to provide these intravenous fluids under pressure to increase the flow rate. The pressure has been provided by several techniques, one of which is to engage a bag containing the fluid with an inflatable bladder. The bladder is inflated by air from a compressor, or another source of pressurized gas, which is connected to the bladder through a control valve.

It is also known to allow deflation of the bladder by a control valve that can be placed in a position whereby it vents the bladder to the atmosphere, such as is shown in U.S. Pat. Nos. 3,640,276 and 4,430,078. It is also known to provide rapid deflation of a bladder by a venturi that produces a lower pressure for pumping the air out of the bladder.

A problem with prior control valves has been to combine rapid deflation, ease of operation, and low manufacturing cost.

SUMMARY OF THE INVENTION

In accordance with the invention, a pressure infusion system includes an inflatable bladder for engaging a flexible bag of physiological fluids, a pump for supplying air under pressure, and a valve for controlling both supply of the pressurized air to the bladder and rapid exit of air from the bladder.

One feature of the invention is the use of a large-bore supply tube connecting the outlet of the control valve to the bladder. The diameter of this tube is much larger than is required to supply the bladder with air, and is made large because the control valve also allows deflation of the bladder through the tube. The increased bore size allows the bladder to deflate very rapidly without further assistance. Thus, the control valve of the invention includes an inlet for receiving air from a pressure pump, an outlet for transmitting air under pressure to the bladder, and a discharge port for allowing rapid discharge of the bladder. In the preferred embodiment, the valve comprises a body portion having a docking port and an outlet port. The body receives a toggle element that is mounted for pivotal movement between these two ports. The toggle includes an inlet port and a channel for communication with the docking port or the outlet port, depending on whether the toggle is in the inflate or deflate position.

When the toggle is in the inflate position the channel is in communication with the outlet port, and air under pressure is supplied to the bladder through the large bore tube. When the toggle is in the deflate position, the channel is in communication with the docking port, and the outlet port is open to the atmosphere. Thus, in the deflate position, the air in the bladder is rapidly discharged to the atmosphere to allow a full bag of fluids to be installed easily.

The invention also includes a method of inflating and deflating an expandable bladder in conjunction with pressurizing a flexible bag of physiological fluid by inflating the expandable bladder by introducing pressurized fluid into the expandable bag first through an inlet channel having a first cross sectional area and then through a supply tube in communication with the expandable bladder. The bladder can then be deflated by bypassing the inlet channel to release the pressurized fluid first through the supply tube and then through an outlet exposed by the bypassing of the inlet channel, the outlet having a second cross sectional area greater then the first cross sectional area of the inlet channel.

It will be appreciated that the valve of the invention is unique in that the inlet port is quite small relative to the outlet port. Similarly, the tubing connecting the air pump to the inlet is much smaller than the supply tube connecting the valve to the bladder.

The system of the invention is preferably implemented by mounting the control valve on the base of the device such that the toggle is easily accessed by an operator. This position is such that the operator can easily move the toggle between inflate and discharge positions while opening or closing the door to the device and exchanging the fluid bags.

DETAILED DESCRIPTION OF THE PREFERRED EMBODIMENT

Figure 1:
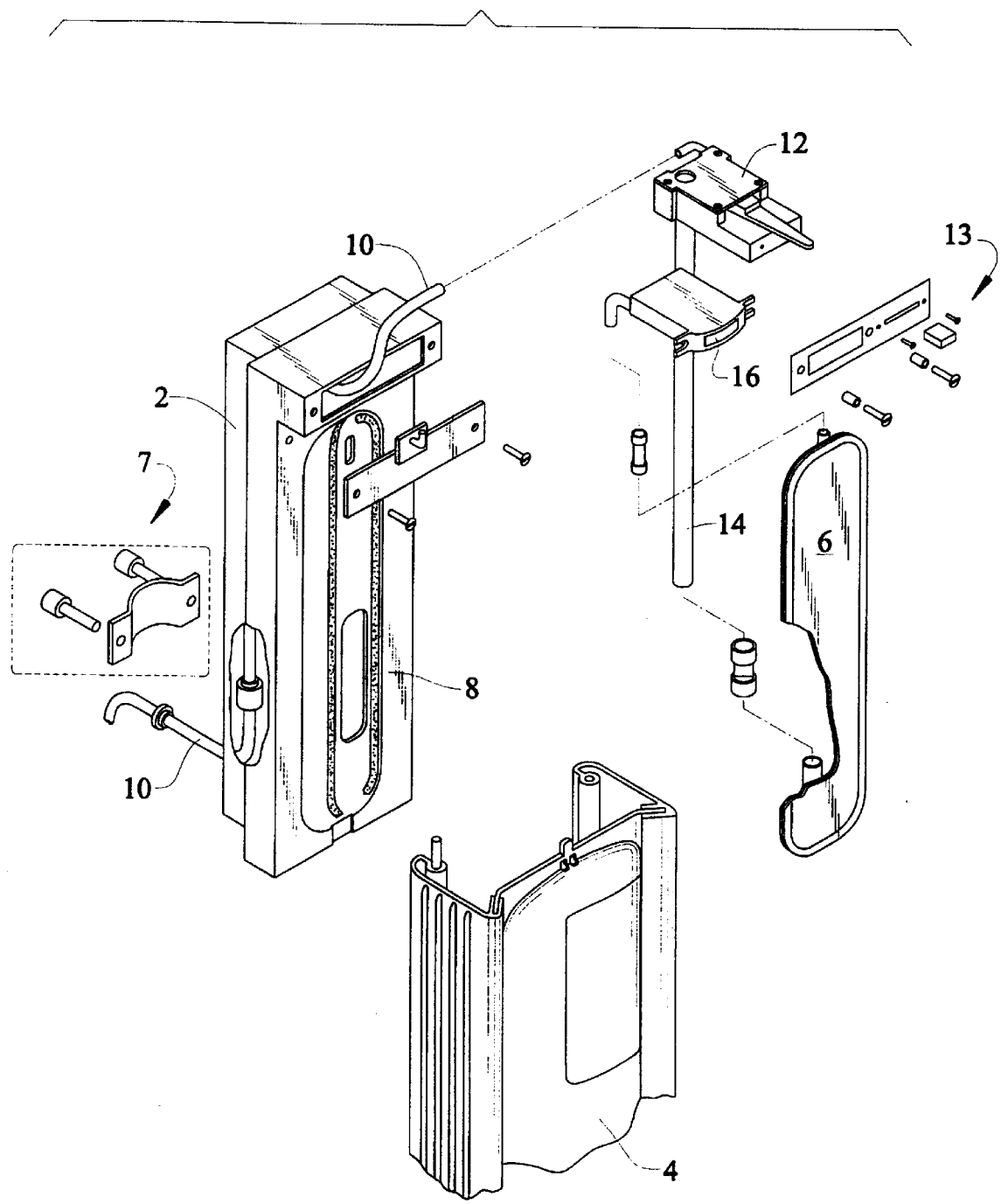
FIG. 1 is a perspective of an infusion system in accordance with the invention.

With reference to FIG. 1, a system in accordance with the invention includes a housing 2 to which a door 4 is pivotally mounted, the housing secured by fastening components 7. A pressure bladder 6 is secured to a depression in a front wall 8 of the housing for engaging a bag of physiological fluids (not shown) held between the bladder and the door. The physiological fluids are connected to a patient as known in the art for infusion. When the bladder is inflated, the volume between the rear wall and the bag decreases, thus applying pressure to the fluids in the bag to infuse the fluids under pressure.

The bladder is inflated by air supplied from a pump (not shown) through an inlet tube 10. The inlet tube is connected to the inlet of a control valve 12, which will be described further below. The outlet of the control valve is connected to a supply tube 14, which is in turn connected to the bladder. A pressure monitor gauge 16 is also connected to the bladder to allow the operator to monitor the bladder pressure. The control valve 12 is secured by fastening assembly components 13.

Figure 2:
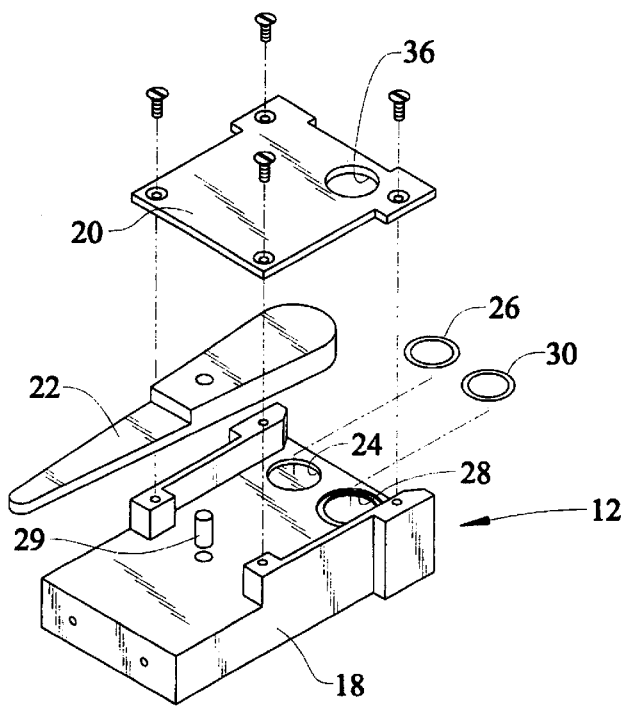
FIG. 2 is an exploded perspective of a control valve in accordance with the invention.

With reference to FIG. 2, the control valve includes a body portion 18 and a cover 20, which form a cavity for receiving a toggle portion 22. As will be described in connection with FIG. 3 the toggle provides an inlet and a connecting channel. The body provides a docking position 24, which is preferably a dead end depression containing an O-ring 26 for sealing the toggle to the floor of the body when the toggle is in the docking position. The body also includes an outlet port 28 and a second O-ring 30 for sealing the toggle to the outlet port when in that position.

Figure 3A:
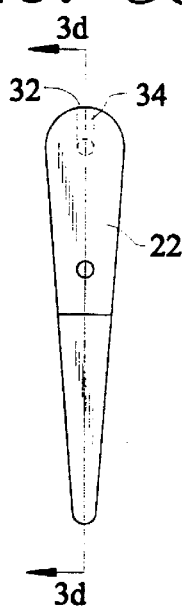
FIGS. 3a through 3d is a series of views detailing the toggle portion of the valve of FIG. 2.
Figure 3B:
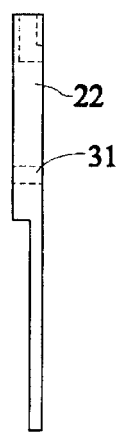
Figure 3C:
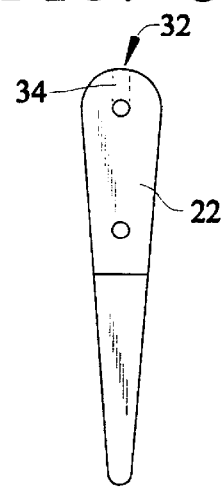
Figure 3D:
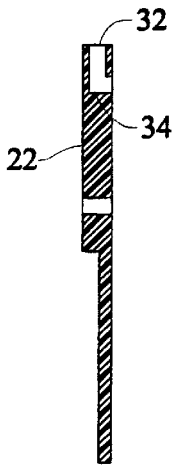

With reference to FIGS. 3a–3d, the toggle includes an inlet 32, which is part of a channel 34. The inlet tube 10 from the pump or other source of pressurized air is attached to the inlet 32 as shown in FIG. 1. The channel 34 communicates the fluid under pressure to the dead end docking port 24 when the toggle is in one position and to the outlet port 28 when the toggle is in a second position. The toggle 22 pivots about pin 29, see FIG. 1, the pin engaging bore 31 as shown in FIG. 3b.

Referring again to FIG. 2, the cover 20 includes an opening 36 aligned with the outlet port 28, and there is a substantial open space above the outlet port 28 between the cover and the floor of the body portion when the toggle is not covering the outlet port.

Thus, the operation of the system is as follows. When the bladder is to be inflated, the operator moves the toggle to the position wherein it covers the outlet port 28. Air from the source of pressurized air flows through the channel 34, through the supply tube 14 and into the bladder. When the operator wishes to change bags of fluid, the toggle is moved to the position where it covers the docking port, which accomplishes two things.

First, moving the toggle to the docking position directs the air from the pump to the dead end, which will automatically shut off the pump as the pressure increases. Secondly, and more importantly, the supply tube will be open to the atmosphere, whereby the bladder will discharge quickly.

In the preferred embodiment, the dimensions of the supply tube are such that there is only negligible pressure drop between the bladder and the atmosphere when in the discharge mode. In other words, the bladder achieves pressure equilibrium with the atmosphere almost instantaneously, thus obviating the necessity of assistance in the discharge. In the preferred embodiment the inside diameter of the supply tube is at least 0.375 inch to provide adequate venting from a normal bladder used of blood bags. The outside diameter may be 0.50 inch or larger. The inside diameter of the inlet tube is preferably about 0.125 inch with an outside diameter of about 0.250 inch.

Modifications within the scope of the appended claims will be apparent to those of skill in the art.

We claim:

1. A control valve for controlling inflation and deflation of a bladder comprising:
   a body having a port for fluid communication with a bladder,
   a toggle mounted to said body for movement between first and second positions and having an inlet for receiving pressurized fluid and a channel communicating with said inlet for conducting said pressurized fluid,
   wherein said port is located in said body to be in fluid communication with said channel when said toggle is said first of said positions and in free communication with the atmosphere when said toggle is in said second of said positions, and wherein said port is larger than said inlet and provides a negligible pressure drop between said bladder and the atmosphere when said toggle is in said second of said positions.

2. A control valve according to claim 1 wherein said toggle is mounted to said body for pivotal movement.

3. A control valve according to claim 2 wherein said body has a cavity for receiving said toggle.

4. A control valve according to claim 1 wherein the cross sectional area of said outlet port is at least about 0.1 in$^2$.

5. A combination comprising a control valve according to claim 1, a bladder, a supply tube connecting said port to said bladder, and an inlet tube for connecting a source of pressurized air to said inlet, and wherein said supply tube has a cross section that is at least as large as said port.

6. A combination according to claim 5 further comprising means for supporting said valve and said bladder and wherein said toggle has an operating lever extending outward of said housing.

7. A combination according to claim 6 further comprising means for supporting a flexible bag of physiological fluids.

8. A control valve according to claim 1 wherein said port is uncovered when said toggle is in said second of said positions.

9. A control valve according to claim 1, wherein the pressurized fluid is shut off when said toggle is moved to said second position.

10. A valve for controlling inflation and deflation of a bladder comprising:
    means forming an outlet port for fluid communication with a bladder, the size of said outlet port being large enough to create no more than a negligible resistance to the flow of a fluid from said bladder, and
    means for selectively communicating a fluid under pressure to said outlet port.

11. A valve according to claim 10 wherein said means forming an outlet port further includes means for mounting said means for selectively communicating a fluid under pressure for pivotal movement between a first position wherein said fluid under pressure is in communication with said outlet port and a second position wherein said outlet port is exposed to the atmosphere.

12. A valve according to claim 10 wherein said means for selectively communicating said fluid under pressure comprises a channel for carrying said fluid under pressure and an inlet to said channel, and said outlet port is larger than said channel and said inlet.

13. A valve according to claim 10 in combination with a bladder, means for housing said bladder and said valve, and means for supporting a flexible bag of physiological fluids in contact with said bladder.

14. In an apparatus for pressurizing a flexible bag of physiological fluids having an expandable bladder, means for supporting said bag of physiological fluids in contact with said bladder, and a source of pressurized fluid, the improvement comprising a control valve connected to said source of pressurized fluid through an inlet of a first cross sectional area and connected to said bladder through an outlet of a second cross sectional area, and a toggle having a channel for effecting a fluid connection between said inlet and said outlet to inflate said bladder when at a first position and for exposing said outlet to the atmosphere to deflate said bladder when at a second position, and wherein said second cross sectional area creates no more than a negligible pressure drop between said bladder and the atmosphere during deflation.

15. An apparatus according to claim 14 wherein said control valve comprises a body having said outlet and wherein said toggle is mounted to said body for movement between said first position where said inlet is in fluid communication with said outlet and said second position where said outlet is exposed to the atmosphere, the pressurized fluid being shut off when said toggle is at said second position.

16. An apparatus according to claim 15 wherein said control valve is pivotally connected to said body.

17. An apparatus of claim 14, wherein said source of pressurized fluid is shut off when said toggle is at said second position.

18. A method of inflating and deflating an expandable bladder in conjunction with pressurizing a flexible bag of physiological fluid comprising:

a) inflating the expandable bladder by moving a control valve member to a first position to connect an inlet channel having a first cross sectional area and a supply tube in communication with the expandable bladder, said inlet channel being part of and movable with said control valve member; and b) deflating the expandable bladder by moving said control valve member to a second position to disconnect said inlet channel and said supply tube and expose the supply tube to atmosphere, the outlet having a second cross sectional area greater then the first cross sectional area of the inlet channel.

19. The method of claim 18, wherein the inlet channel is moved with respect to the outlet.

20. The method of claim 18, wherein the second cross sectional area is such that deflation occurs with a minimum of pressure drop between said bladder and the atmosphere.

* * * * *